(12) United States Patent
Berman et al.

(10) Patent No.: US 8,815,610 B2
(45) Date of Patent: Aug. 26, 2014

(54) MAGNETIC NANOPARTICLE DETECTION ACROSS A MEMBRANE

(75) Inventors: David Berman, San Jose, CA (US); Qiu Dai, Sunnyvale, CA (US); William Marvin Dyer, San Jose, CA (US); Wayne Isami Imaino, San Jose, CA (US); Alshakim Nelson, Fremont, CA (US)

(73) Assignee: International Business Machines Corporation, Armonk, NY (US)

( * ) Notice: Subject to any disclaimer, the term of this patent is extended or adjusted under 35 U.S.C. 154(b) by 785 days.

(21) Appl. No.: 12/905,994

(22) Filed: Oct. 15, 2010

(65) Prior Publication Data

US 2012/0094852 A1    Apr. 19, 2012

(51) Int. Cl.
*G01N 33/553* (2006.01)
*G01N 33/543* (2006.01)

(52) U.S. Cl.
CPC .............................. *G01N 33/54326* (2013.01)
USPC .......................................... 436/526; 436/518

(58) Field of Classification Search
USPC ................................................. 436/526, 518
See application file for complete search history.

(56) References Cited

U.S. PATENT DOCUMENTS

| | | | | |
|---|---|---|---|---|
| 4,452,773 | A * | 6/1984 | Molday | 424/1.37 |
| 6,124,139 | A * | 9/2000 | Saito et al. | 436/539 |
| 6,607,922 | B2 * | 8/2003 | LaBorde | 436/514 |
| 7,048,890 | B2 | 5/2006 | Coehoorn et al. | |
| 7,504,262 | B2 * | 3/2009 | Fox | 436/149 |
| 7,682,838 | B2 | 3/2010 | Wang et al. | |
| 2004/0253744 | A1 | 12/2004 | Rife et al. | |
| 2005/0100930 | A1 | 5/2005 | Wang et al. | |
| 2007/0122898 | A1 | 5/2007 | Sharma | |
| 2007/0231926 | A1 * | 10/2007 | Ikeda | 436/526 |
| 2008/0221806 | A1 | 9/2008 | Bryant et al. | |
| 2008/0318342 | A1 * | 12/2008 | Durack et al. | 436/526 |
| 2009/0021250 | A1 | 1/2009 | Ikeda | |
| 2009/0065359 | A1 | 3/2009 | Zhou | |
| 2009/0186770 | A1 | 7/2009 | Shi et al. | |

FOREIGN PATENT DOCUMENTS

| | | |
|---|---|---|
| EP | 2060637 A1 | 5/2009 |
| WO | 03/054523 A2 | 7/2003 |
| WO | 2007/092909 A2 | 8/2007 |

(Continued)

OTHER PUBLICATIONS

Guanxiong Li et al., "Spin valve sensors for ultrasensitive detection of superparamagnetic nanoparticles for biological applications", Sensors and Actuators 2006, vol. A, No. 126, pp. 98-106.

(Continued)

*Primary Examiner* — Bao Thuy L Nguyen
*Assistant Examiner* — Pensee Do
(74) *Attorney, Agent, or Firm* — Daniel E. Johnson

(57) ABSTRACT

Magnetic nanoparticles are detected across a thin membrane that separates the nanoparticles from a magnetic sensor. The technique can be used in a medical context, in which an analyte of interest (present in a test fluid, such as blood) is attached to the membrane. Other compounds are in turn bound to the analyte, with one of these compounds including a magnetic nanoparticle that is then detected by the sensor. In this way, the analyte is detected by detecting the magnetic nanoparticle. By counting the number of magnetic nanoparticles, the concentration of the analyte in the test fluid can be determined.

22 Claims, 7 Drawing Sheets

(56) References Cited

FOREIGN PATENT DOCUMENTS

| WO | 2009/029859 A2 | 3/2009 |
| WO | 2009/039437 A1 | 3/2009 |
| WO | 2009/071404 A1 | 6/2009 |

OTHER PUBLICATIONS

Guanxiong Li et al., "Detection of single micron-sized magnetic bead and magnetic nanoparticles using spin valve sensors for biological applications", Journal of Applied Physics May 2003, vol. 93, No. 10, pp. 7557-7559.

John Nordling et al., "Giant Magnetoresistance Sensors. 1. Internally Calibrated Readout of Scanned Magnetic Arrays", Analytical Chemistry Nov. 2008, vol. 80, No. 21, pp. 7930-7939.

Rachel L. Millen et al., "Giant Magenetoresistive Sensors. 2. Detection of Biorecognition Events at Self-Referencing and Magnetically Tagged Arrays", Analytical Chemistry Nov. 2008, vol. 80, No. 21, pp. 7940-7946.

Sining Mao et al., "Commercial TMR Heads for Hard Disk Drives: Characterization and Extendibility At 300 Gbit/in2", IEEE Transactions on Magnetics Feb. 2006, vol. 42, No. 2, pp. 97-102. Digital Object Identifier 10.1109/TMAG.2005.861788.

Richard S. Gaster et al., "Matrix-insensitive protein assays push the limits of biosensors in medicine", Nature Medicine Oct. 2009, pp. 1-7.

Qiu Dai et al., "Self-Assembled Ferrimagnet-Polymer Composites for Magnetic Recording Media", Nano Letters 2010, vol. 10, pp. 3216-3221.

Balasubramanian Srinivasan et al., "A Detection System Based on Giant Magnetoresistive Sensors and High-Moment Magnetic Nanoparticles Demonstrates Zeptomole Sensitivity: Potential for Personalized Medicine", Angew. Chem. Int. Ed. 2009, vol. 48, pp. 2764-2767.

A.J. Argumedo et al., "Scaling tape-recording areal densities to 100 Gb/in2", IBM J. Res. & Dev. vol. 52, No. 4/5 Jul./Sep. 2008, pp. 513-527.

Sebastian J. Osterfeld et al., "Multiplex protein assays based on real-time magnetic nanotag sensing", The National Academy of Sciences of the USA Dec. 2008, vol. 105, No. 52, pp. 20637-20640.

Liang Xu et al., "Giant magnetoresistive biochip for DNA detection and HPV genotyping", Biosensors and Bioelectronics 2008, vol. 24, pp. 99-103.

PCT International Search Report Dated Dec. 27, 2011, PCT Application No. PCT/EP2011/067516.

\* cited by examiner

US 8,815,610 B2

MAGNETIC NANOPARTICLE DETECTION ACROSS A MEMBRANE

TECHNICAL FIELD

The invention relates to detecting magnetic particles, and more particularly, to detecting magnetic nanoparticles for medical and biological sensor applications.

BACKGROUND

There is an ongoing need to analyze biological analytes accurately, quickly, and at reasonable cost. Indeed, the extent to which this can be done is one measure of a health care system's ability to provide satisfactory health care. An improvement in the ability to detect biomarkers would be beneficial in a variety of medical endeavors, such as the detection of cancer and other diseases.

A variety of techniques are currently used to detect analytes, in which analytical chemistry methods are employed to identify specific compounds of interest to a medical practitioner. An immunoassay is a biochemical test used to detect or measure the concentration of a chemical compound in a solution; it relies on the ability of antigens and antibodies to bind to each other with a high degree of specificity. Immunoassays can be employed to detect either the antigen or its corresponding antibody. One kind of immunoassay is the magnetic immunoassay, in which antigens and antibodies are bound to each other, and magnetic particles are then attached to the antigens (or antibodies) of the antigen/antibody pairs. The magnetic particles are then detected with a magnetic detection apparatus, thereby providing an indication of the concentration of the analyte of interest (e.g., the antigen or the antibody). By tagging analytes with magnetic nanoparticles, the problem of biological detection is in effect reduced to one of magnetic field measurement.

One magnetic immunoassay method involves scanning a giant magnetoresistance (GMR) sensor at a relatively large distance of several microns above a biological test sample. (See, for example, J. Nordling et al., "Giant Magnetoresistance Sensors. 1. Internally Calibrated Readout of Scanned Magnetic Arrays," Anal. Chem., 80 (21), pp. 7930-7939, 2008; and R. L. Millen et al., "Giant Magnetoresistive Sensors. 2. Detection of Biorecognition Events at Self-Referencing and Magnetically Tagged Arrays," Anal. Chem., 80 (21), pp. 7940-7946, 2008.) With this method, a relatively large distance between the sensor and the test sample is required, since the sample is typically fragile and would be easily damaged by the sensor. As a result, the magnetic particles must be correspondingly large to produce a sufficiently strong magnetic field at this distance. Accordingly, the spatial resolution that can be achieved is relatively poor. Also, large magnetic particles may require a greater number of analytes to join them to a functionalized sample surface, thereby decreasing the detection sensitivity.

In another magnetic immunoassay method, the analytes and magnetic particles are located directly on the GMR sensors' surface. (See, for example, G. Li et al., "Detection of single micron-sized magnetic bead and magnetic nanoparticles using spin valve sensors for biological applications," Journal of Applied Physics, vol. 93 (10), 2003; and U.S. Pat. No. 7,682,838 to Wang et al. titled "Magnetic Nanoparticles, Magnetic Detector Arrays, and Methods for their Use in Detecting Biological Molecules".) With a dedicated sensor being used for each test site and the magnetic particles being located at the sensor surface, the field sensitivity is quite high. On the other hand, this means that to process a large number of different analytes, it is necessary to have a very complicated test chip that includes a correspondingly large number of GMR sensors dedicated to respective test sites and analytes.

SUMMARY

Methods are disclosed herein in which a test fluid is examined for an analyte (or multiple analytes) of interest. A thin but robust membrane serves as a protective layer for the analyte while also defining the spacing between magnetic particles (that are selectively attached to the analyte) and a magnetic sensor. The magnetic sensor and the analyte are located on opposite sides of this membrane.

In one exemplary implementation, antibodies that match (i.e., that specifically bind to) an antigen of interest are functionalized and attached to a thin membrane. A test fluid, such as blood from a patient, having the antigen of interest therein is then passed over the membrane to which the antibodies have been attached. The result is that the antigen of interest in the test fluid specifically binds to the antibodies (whereas other kinds of antigens in the test fluid are not bound to those antibodies). At this point, the membrane may be rinsed (e.g., high purity water may be used), leaving behind the functionalized antibodies and bound antigens. Antibodies (of the same kind as those attached to the membrane) to which magnetic nanoparticles have been previously attached are now passed over the membrane, so that the bound antigens specifically attach to these antibody/magnetic nanoparticle structures, which is followed by another rinse (e.g., using high purity water). The result now is a collection of sandwich structures, each consisting of an antibody functionalized to the membrane, an antigen attached to this antibody, and another antibody of the same kind attached to the antigen on one end and to a magnetic nanoparticle on the other end. Magnetic nanoparticles can only be captured when the antigen of interest is present in the test fluid, and the number of captured magnetic nanoparticles is indicative of the concentration of the antigen of interest in the test fluid. The magnetic nanoparticles are detected with a magnetic detection apparatus, which is scanned across that side of the membrane opposite the side where the magnetic nanoparticles are joined to the membrane.

One aspect of the invention is a method for use with magnetic particles (or even just one magnetic particle) joined to a first side of a membrane, with each of the magnetic particles being bound to an analyte of interest. The method includes detecting the magnetic particles using a magnetic sensor located on a second side of the membrane (that is opposite to the first side), in which the magnetic sensor moves relative to the membrane. The method preferably includes counting the number of the magnetic particles. The sensor may be scanned along the second side of the membrane, thereby determining the positions of the magnetic particles. The membrane preferably has a thickness of less than 100 nanometers, and more preferably less than 50 nanometers, whereas the magnetic particles preferably have a characteristic dimension of less than 100 nm. The magnetic particles are advantageously ferromagnetic or ferrimagnetic, and may be arranged in an array.

Another aspect of the invention is a method for use with a membrane having an array of regions on a first side of the membrane, with each of the regions having a plurality of reaction sites. The method includes functionalizing the reaction sites, so that reaction sites in different regions have different capture antibodies. The method further includes applying a test fluid to the first side of the membrane, with the test fluid including different antigens, so that antigens specifically bind to certain ones of the capture antibodies. The method also includes applying, to the bound antigens, a solution of magnetic particles functionalized with antibodies corresponding to the bound antigens, so that at least some of the bound antigens are joined to respective magnetic particles functionalized with antibodies, resulting in magnetic particles being joined to respective reaction sites. At least one sensor is scanned along a second side of the membrane (that is opposite to the first side), to determine the number of magnetic particles in each region that are joined to reaction sites. Once this is known, the concentrations of the antigens in the test fluid may be determined. Also, a sealant may be applied over the first side of the membrane, so that the magnetic particles are secured.

Yet another aspect of the invention is a method for use with a membrane having reaction sites on a first side of the membrane. The method includes functionalizing the reaction sites, so that the reaction sites have an affinity for an analyte of interest. The method further includes applying a test fluid to the first side of the membrane, in which the test fluid includes the analyte of interest, with the analyte binding to reaction sites on the first side of the membrane. The method also includes applying, to the first side of the membrane having the bound analyte, a solution of magnetic particles functionalized with a compound that has an affinity for the analyte, so that magnetic particles are joined to reaction sites on the first side of the membrane. At least one sensor is then scanned along a second side of the membrane (that is opposite to the first side), to determine the number of magnetic particles joined to reaction sites on the first side of the membrane.

BRIEF DESCRIPTION OF THE DRAWINGS

FIG. 3, which includes

DETAILED DESCRIPTION

Figure 1:
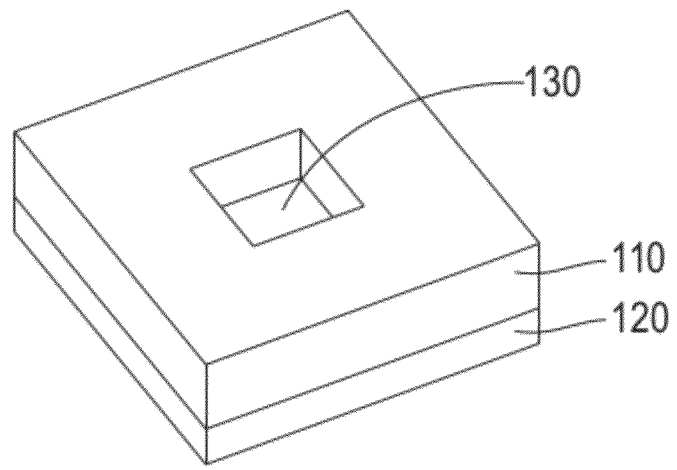
FIGS. 1 and 2 illustrate a device used for receiving test fluid (that includes an analyte of interest to be detected).
Figure 2:
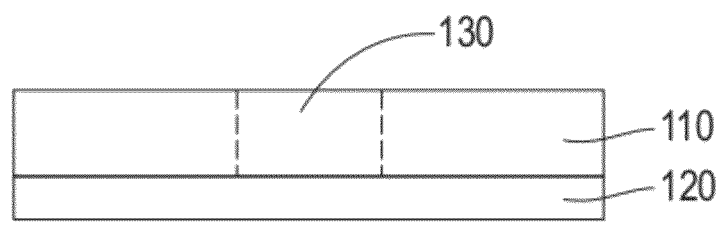

Preferred methods are now discussed with respect to the various figures. FIG. 1 shows a "chip" 110 to which a thin membrane 120 is attached. The chip may be made of Si, for example. The membrane 120, on the other hand, may be made of carbon, a polyvinyl resin (e.g., a polyvinyl alcohol), SiN, Si, or $SiO_2$, for example. The membrane is relatively thin, e.g., it may be 5 nm thick, or up to 15 nm thick, but is preferably not thicker than 100-200 nm. The chip 110 has a centrally located cavity 130 therein through which a portion of the membrane 120 can be seen. The chip 110/membrane 120 structure may be formed by beginning with a Si block and depositing a film of SiN onto it. The cavity 130 may be formed by etching through the chip 110 until the membrane 120 is reached. The cavity 130 may have areal dimensions of 100 microns×100 microns, or even 1 mm×1 mm. FIG. 2 is a cross-sectional view of the structure shown in FIG. 1. The device shown in FIGS. 1 and 2 is commercially available (e.g., from SiMPore, Inc. or Ted Pella, Inc.), since it can be used in the high resolution microscopy industry as a substrate onto which a substance can be placed.

Figure 3A:
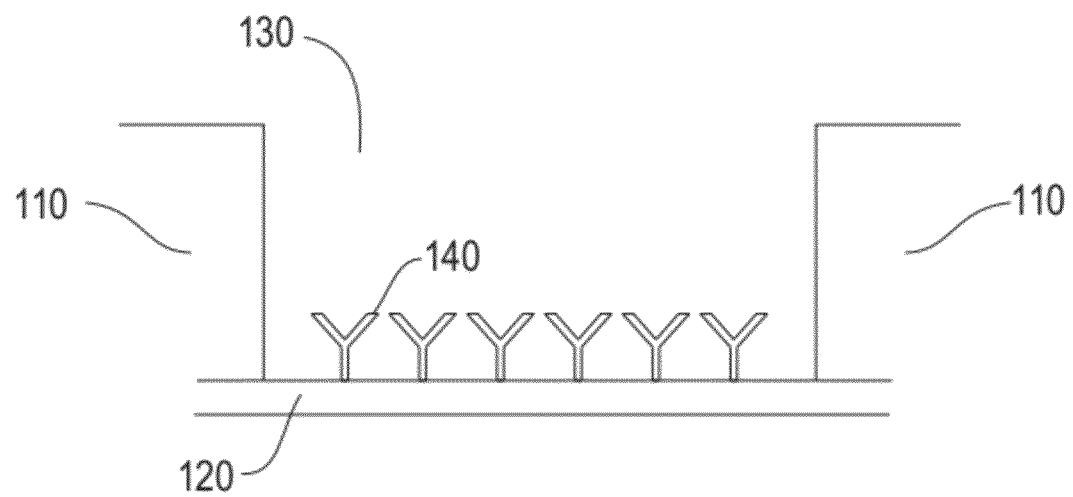
FIGS. 3A, 3B, and 3C, illustrate a series of steps in which the analyte is bound to the underlying membrane of the device, and molecular species (one of which includes a magnetic nanoparticle) are in turn attached to the bound analyte.

FIG. 3 is a schematic representation of how magnetized sandwich structures can be built up on the membrane 120, with each of these structures including an antigen of interest and a magnetized nanoparticle that can be detected by a magnetic sensor. The antigen of interest may be any one of a number of analytes, such as a biomarker (e.g., a protein indicating the presence of cancer). Antibodies are first bound to the membrane 120 using methods known to those skilled in the art (see, for example, Osterfeld et al., "Multiplex protein assays based on real-time magnetic nanotag sensing", *Proc. Natl. Acad. Sci. USA*, v. 105, pp. 20637-20640, 2008). In particular, a solution is prepared that includes antibodies that specifically bind to the antigen of interest. This solution is brought into contact with the membrane 120, resulting in antibodies 140 attaching themselves to the membrane, as shown in FIG. 3A. Only six such antibodies 140 are shown in FIG. 3A for the sake of clarity, although typically in practice potentially millions or more of such antibodies would be attached to the membrane 120.

Figure 3B:
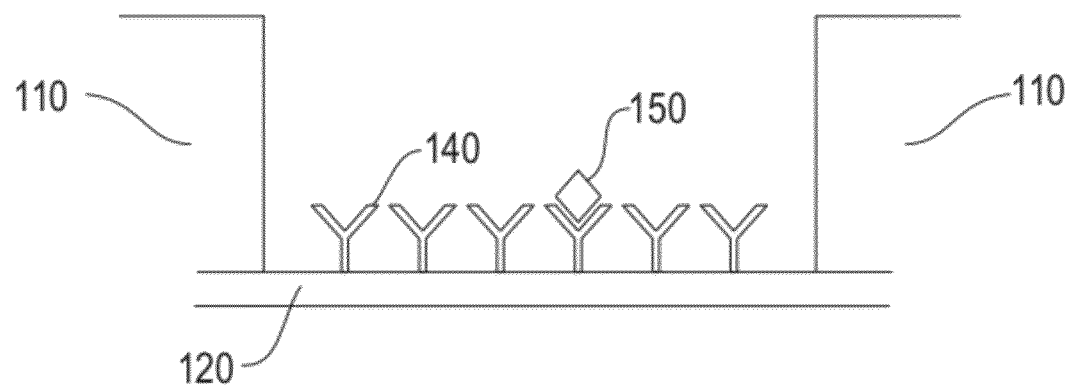
Figure 3C:
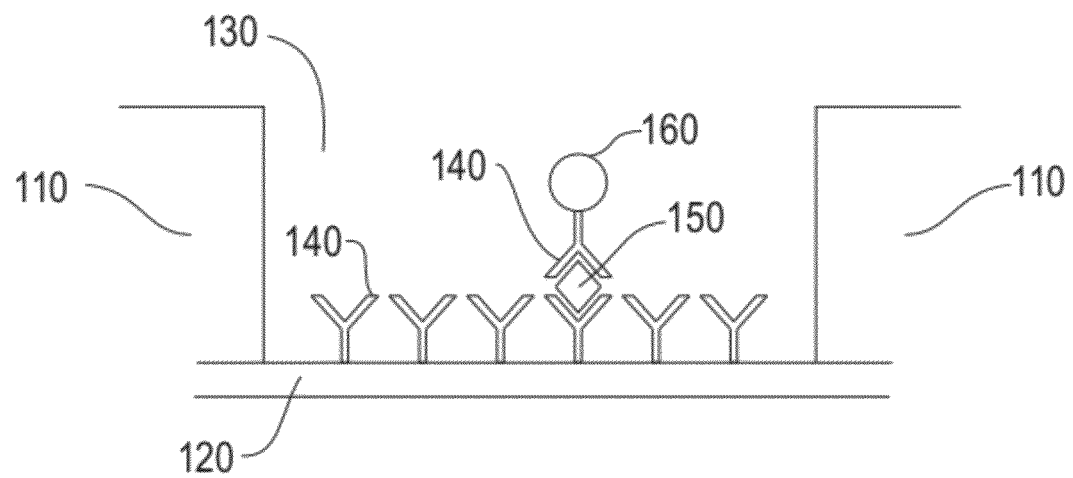

After an optional rinse is applied over the membrane, test fluid (such as blood from a patient) is then brought into contact with the antibodies 140. For purposes of this discussion, the fluid is assumed to include the antigen of interest (since if it does not, none of the magnetized sandwich structures referred to above will be formed). When an antigen of interest comes into contact with one of the antibodies 140 bound to the membrane 120, it binds to that antibody since the antigen and antibody have a specific affinity for each other. FIG. 3B shows a resulting antigen/antibody pair, in which an antigen of interest 150 is bound to one of the antibodies 140. Only one antigen/antibody pair is shown in this figure for the sake of clarity, although in practice many such pairs can be formed. Indeed, there are ideally more antibodies 140 (attached to the membrane 120) than there are antigens 150 in the test fluid, so that all of the antigens of interest in the fluid can be captured. (Other antigens in the test fluid would not be expected to be captured by the antibodies 140, since they would not have the required affinity for each other.) At this point, another optional rinse may be applied to the membrane.

Once the antigen of interest has been captured, the problem becomes how to "flag" these captured antigens so that they can be identified later. To this end, an additional solution is employed, which includes antibodies (of the same type as those shown in FIGS. 3A and 3B) that have been bound to respective magnetic nanoparticles, thereby forming antibody/nanoparticle pairs. The magnetic nanoparticles can be functionalized using methods known to those skilled in the art (see, for example, Srinivasan et al., "A Detection System Based on Giant Magnetoresistive Sensors and High-Moment Magnetic Nanoparticles Demonstrates Zeptomole Sensitivity: Potential for Personalized Medicine", *Angew. Chem. Int. Ed.*, v. 48, pp. 2764-2767, 2009). The magnetic particles preferably have an average diameter that is less than 100 nm, e.g., 10-30 nm. The solution with these antibody/nanoparticle pairs is brought into contact with the structures shown in FIG. 3B, so that the antibody portion of the pair "mates" with the antigen 150 to form a sandwich structure that includes a magnetic nanoparticle 160 (see FIG. 3C). A magnetic field (not shown) may be used to facilitate this process by speeding the magnetic nanoparticles 160 towards the antigens 150 and to align the magnetic moment (not shown) of the nanoparticles 160 along a preferred axis (e.g., perpendicular to the membrane 120). Another rinse may now be applied to the membrane. In addition, it may be advantageous to "freeze" in place the structures shown in FIG. 3C by introducing epoxy (e.g., "5 Minute® Epoxy" may be used) into the empty spaces within the cavity 130. Doing this will provide support to the membrane 120 while scanning and will keep the magnetic nanoparticles in a fixed position. In addition, the sealant may be advantageously applied with pressure sufficient to smooth out any undulations in the membrane. Although FIG. 3 has been described with respect to forming a sandwich that includes an antibody/antigen/antibody/nanoparticle structure, analogous methods may be employed to form antigen/antibody/antigen/nanoparticle structures.

Figure 4:
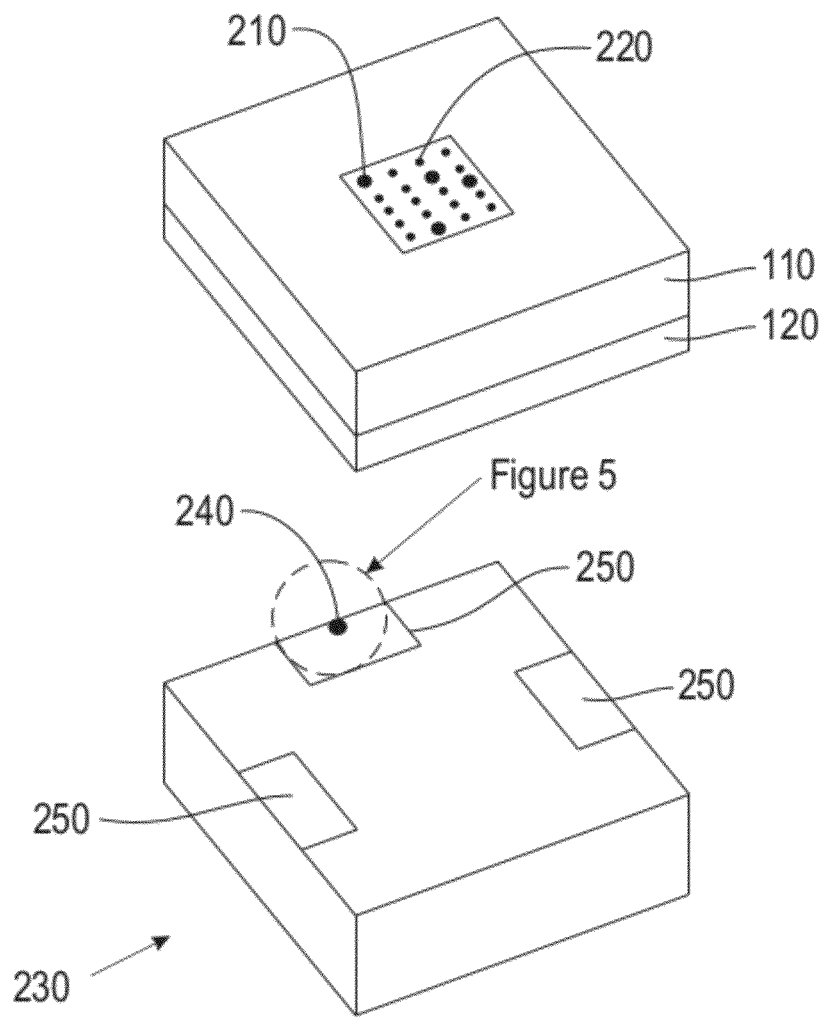
FIG. 4 shows magnetic nanoparticles joined to the device as a result of these steps, as well as a magnetic sensor device for detecting the magnetic nanoparticles.

The result of the process just described in connection with FIG. 3 is illustrated schematically in FIG. 4. In contrast to FIG. 1, FIG. 4 shows a number of reaction sites 210 where the magnetic nanoparticles 160 are located. Additional reaction sites 220 are also shown corresponding to antibodies 140 that did not bind to an antigen 150. The task now becomes counting the number of magnetic nanoparticles 160, which is most easily done with the help of a magnetic sensor device 230. (Once the number of magnetic nanoparticles 160 is determined, the concentration of the antigen in the test fluid can be determined by dividing this number by the volume of the test fluid introduced into the cavity 130.) The sensor device 230 may include, for example, a giant magnetoresistance (GMR) sensor element 240 that is advantageously located within one of a number of pads 250 integrally formed from a block of material, e.g., AlTiC. (Other magnetoresistance sensor elements, such as a tunneling magnetoresistance element, may be used.) The pads 250 are preferably smooth (e.g., they may even be of "air-bearing" quality), so that the sensor device 230 may be scanned underneath and in contact with the membrane 120.

Figure 5:
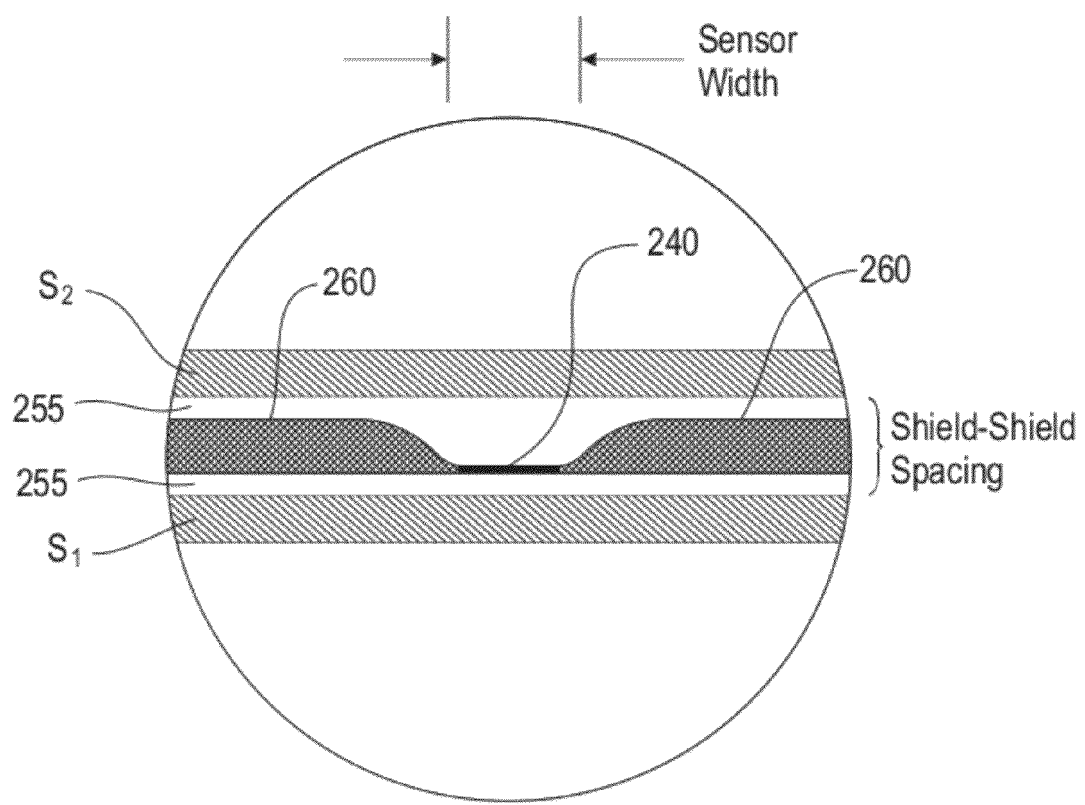
FIG. 5 shows a magnetic sensor element of the magnetic sensor device.

The sensor element 240 may be a conventional GMR element, e.g., such as that described in U.S. Pat. No. 5,159,513 titled "Magnetoresistive sensor based on the spin valve effect". FIG. 5 shows a plan view of one such sensor element 240 and its adjoining components. The sensor element 240 is electrically insulated by regions 255 (made of $Al_2O_3$, for example) which are in turn bracketed by permalloy regions S1 and S2. Lead lines 260 are connected to both sides of the sensor element 240. A distance in the range of 30-120 nm, for example, may separate S1 and S2 (the shield-to-shield spacing). The sensor element 240 may have dimensions of 40-100 nm (the sensor width) by 5-10 nm (the sensor thickness), so that a magnetic nanoparticle having a diameter of 100 nm can be easily resolved. The sensor width is a significant factor in determining the spatial resolution in one dimension, whereas the shield-to-shield spacing is a significant factor in determining the spatial resolution in the orthogonal dimension.

Figure 6:
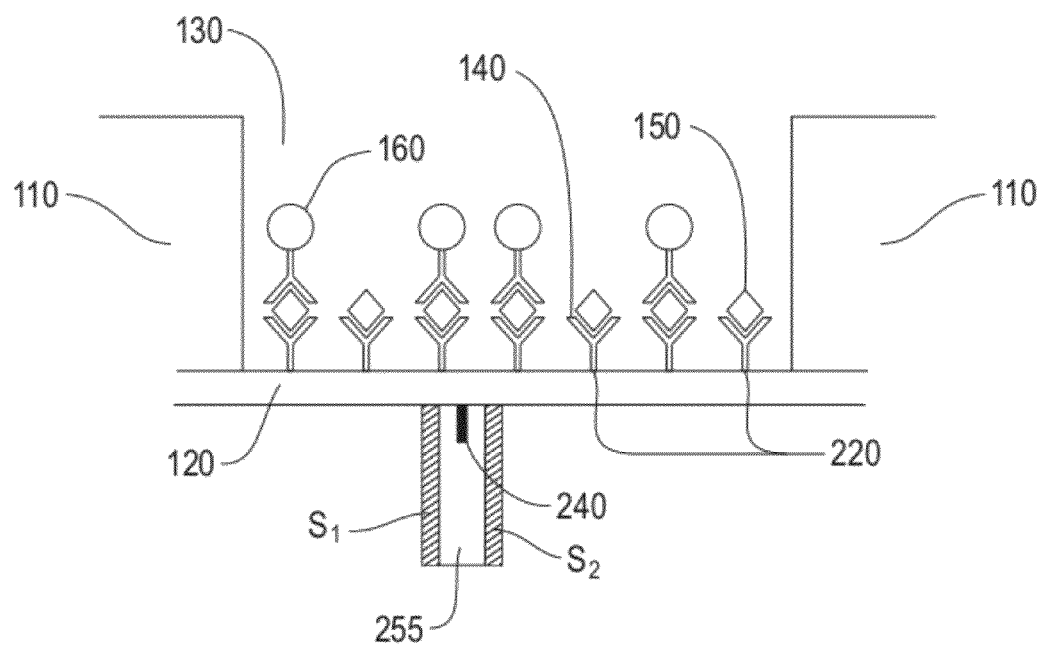
FIG. 6 shows the magnetic nanoparticles being detected by the magnetic sensor device.

FIG. 6 illustrates how magnetic nanoparticles 160 may be detected with the sensor element 240. Sandwich structures are shown that include respective antibodies 140, antigens 150, and magnetic particles 160. Reaction sites 220, which are not joined to a magnetic nanoparticle, are also identified. The sensor element 240 is preferably brought into contact with the membrane 120 (or as close to the membrane as is practicable, e.g., the sensor element 240 may have a thin protective coating affixed thereon), so that it can detect the magnetic nanoparticles 160 located on the other side of the membrane. By scanning back and forth along the membrane 120, the magnetic sensor element 240 detects each of the magnetic nanoparticles 160 (and in so doing detects each of the captured antigens 150). To the extent that the membrane 120 is thin, the detection sensitivity is enhanced, since the magnetic sensor element 240 will be closer to the magnetic nanoparticles 160. For this reason, the thickness of the membrane 120 is preferably no greater than 5-15 nm.

Figure 7:
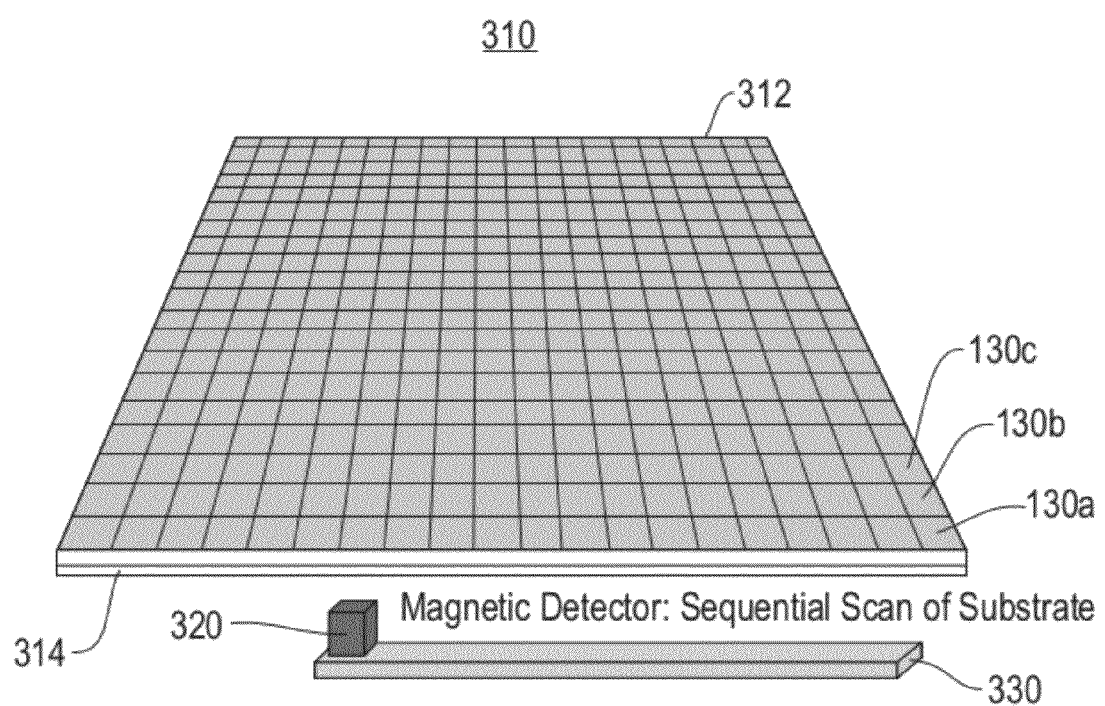
FIG. 7 shows an array of the devices illustrated in FIG. 1.

The cavity 130 shown in FIGS. 1 and 2 (see also FIGS. 3-4 and 6) represents a region in which a number of reaction sites are present, with some of these being functionalized with antibodies designed to capture a specific antigen (or alternatively, reaction sites can be functionalized with antigens designed to capture a specific antibody). As shown in FIG. 7, a number of such regions (130a, 130b, 130c, etc., which may have a rectangular or square shape having an area of $10^4$ square microns, for example) may form a matrix 310, in which each one of the regions is prepared with a different antibody (or antigen). In this manner, test fluid may be screened for a variety of antigens (or antibodies) in parallel.

A magnetic sensor 320 may be scanned back and forth across the various regions that form the matrix 310, with the help of a piezoelectric nanopositioning stage (not shown) connected to a suspension 330 to which the magnetic sensor is attached. The stage 330 may move the magnetic sensor 320 from one end of the matrix 310 to the opposite end of the matrix, and then be stepped incrementally to one side, before scanning the length of the matrix again. Alternatively, a plurality of magnetic sensors (not shown) may be used to scan these regions, e.g., one magnetic sensor may be dedicated to each region 130a, 130b, 130c, etc.

In analogy with how the single cavity device of FIG. 1 is made, the matrix 310 of FIG. 7 may be formed by beginning with a Si block to which a film of SiN has been deposited. The Si block may be photolithographically patterned and then etched through, stopping at the SiN film. The result is an array of cavities within a Si chip 312, each of which is bounded on one side by a SiN membrane 314. Like the device shown in FIG. 1, epoxy may be used to seal magnetized nanoparticles that are attached to an analyte within a cavity, thereby permitting a patient's sample to be archived and retested. The various regions 130a, 130b, 130c, just like their counterpart 130, may have an areal dimension of, for example, 50-500 microns×50-500 microns, corresponding to that portion of the membrane 314 that is exposed.

EXAMPLE

Figure 8:
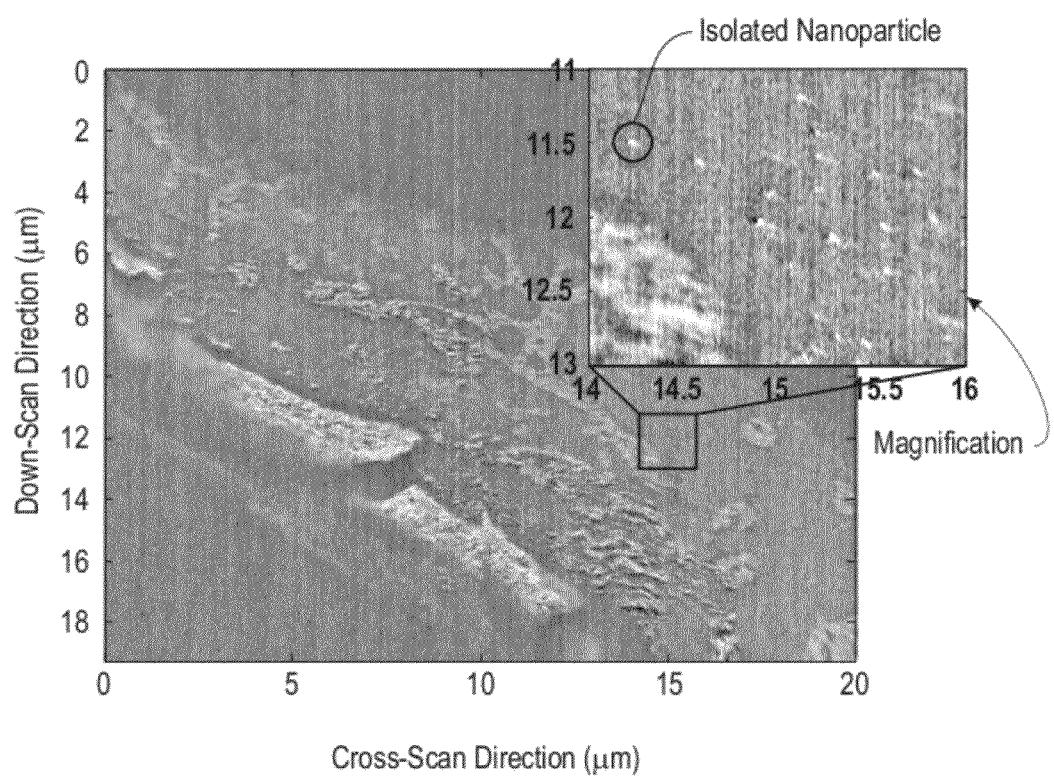
FIG. 8 shows the results of scanning underneath a membrane on which magnetic nanoparticles have been placed.

Ferrimagnetic $CoFe_2O_4$ nanoparticles having a diameter of approximately 18 nm were placed over a SiN membrane having a thickness of 15 nm. The magnetic nanoparticles had been previously coated to hinder aggregation of the nanoparticles, as described in Q. Dai et al., "Self-Assembled Ferrimagnet-Polymer Composites for Magnetic Recording Media", NanoLetters, v. 10, p. 3216, 2010. (This technique permits ferromagnetic and/or ferromagnetic nanoparticles to be employed, in contrast to the superparamagnetic particles of the prior art.) The magnetic nanoparticles were then sealed in place using epoxy. A GMR read sensor was scanned on the opposite side of the SiN membrane. FIG. 8 shows magnetic signal strength as a function of position obtained from such a scan, in which the data are presented in gray scale. The magnified portion in FIG. 8 shows regions having clusters of magnetic nanoparticles, as well as several isolated, individual magnetic nanoparticles, one of which is called out in the inset.

The number of magnetic nanoparticles in a cluster could in principle be determined from the 2-D image of the magnetic field using linear system analysis methods. For example, the magnetic response to a single magnetic nanoparticle could be determined in a control experiment, e.g., using high resolution microscopy (such as TEM) to identify a region where a single magnetic nanoparticle is located. This information could then be used to ascertain the number of particles in any cluster.

The invention may be embodied in other specific forms without departing from its spirit or essential characteristics. The described embodiments are to be considered in all respects only as illustrative and not restrictive. The scope of the invention is therefore indicated by the appended claims rather than the foregoing description. All changes within the meaning and range of equivalency of the claims are to be embraced within that scope.

The invention claimed is:

1. A method for use with magnetic particles joined to a first side of a membrane, each of the magnetic particles being bound to an analyte of interest, the method comprising:
   detecting the magnetic particles using a magnetic sensor located on a second side of the membrane (that is opposite to the first side), wherein the magnetic sensor moves relative to the membrane and scanning the sensor along the second side of the membrane, thereby determining the positions of the magnetic particles.

2. The method of claim 1, comprising counting the number of the magnetic particles.

3. The method of claim 1, wherein the membrane has a thickness of less than 100 nanometers.

4. The method of claim 1, wherein the magnetic particles have a characteristic dimension of less than 100 nm.

5. The method of claim 1, wherein each of the magnetic particles is ferromagnetic or ferrimagnetic.

6. The method of claim 1, wherein an array of magnetic particles is on the first side of the membrane, and each of the magnetic particles is ferromagnetic or ferromagnetic.

7. The method of claim 6, comprising scanning the sensor back and forth along the second side of the membrane, thereby determining the positions of the magnetic particles.

8. The method of claim 7, comprising counting the number of the magnetic particles.

9. A method for use with a membrane having an array of regions on a first side of the membrane, each of the regions having a plurality of reaction sites, the method comprising:
   functionalizing the reaction sites, so that reaction sites in different regions have different capture antibodies;
   applying a test fluid to the first side of the membrane, the test fluid including different antigens, so that antigens specifically bind to certain ones of the capture antibodies;
   applying, to the bound antigens, a solution of magnetic particles functionalized with antibodies corresponding to the bound antigens, so that at least some of the bound antigens are joined to respective magnetic particles functionalized with antibodies, resulting in magnetic particles being joined to respective reaction sites; and
   scanning at least one sensor along a second side of the membrane (that opposite to the first side), to determine the number of magnetic particles in each region that are joined to reaction sites.

10. The method of claim 9, comprising applying a sealant over the first side of the membrane.

11. The method of claim 9, comprising determining the concentration of at least one of the antigens in the test fluid.

12. The method of claim 9, wherein the membrane has a thickness of less than 100 nanometers.

13. The method of claim 9, wherein the magnetic particles have a characteristic dimension of less than 100 nm.

14. The method of claim 9, wherein each of the magnetic particles is ferromagnetic or ferrimagnetic.

15. A method for use with a membrane having reaction sites on a first side of the membrane, the method comprising:
   functionalizing the reaction sites, so that the reaction sites have an affinity for an analyte of interest;
   applying a test fluid to the first side of the membrane, the test fluid including the analyte of interest, the analyte binding to reaction sites on the first side of the membrane;
   applying, to the first side of the membrane having the bound analyte, a solution of magnetic particles functionalized with a compound that has an affinity for the analyte, so that magnetic particles are joined to reaction sites on the first side of the membrane; and
   scanning at least one sensor along a second side of the membrane (that is opposite to the first side), to determine the number of magnetic particles joined to reaction sites on the first side of the membrane.

16. The method of claim 15, comprising applying a sealant over the first side of the membrane.

17. The method of claim 15, comprising determining the concentration of the analyte in the test fluid.

18. The method of claim 15, wherein the membrane has a thickness of less than 100 nanometers.

19. The method of claim 15, wherein the magnetic particles have a characteristic dimension of less than 100 nm.

20. The method of claim 15, wherein each of the magnetic particles is ferromagnetic or ferrimagnetic.

21. A method, comprising:
   providing at least one magnetic particle that is joined to a first side of a membrane, said at least one magnetic particle being bound to an analyte of interest; and
   detecting said at least one magnetic particle using a magnetic sensor located on a second side of the membrane (that is opposite to the first side), wherein the magnetic sensor moves relative to the membrane and scanning the sensor along the second side of the membrane, thereby determining the positions of the magnetic particles.

22. The method of claim 21, said at least one magnetic particle having magnetism selected from the group consisting of ferromagnetism and ferrimagnetism.

* * * * *